US00PP09531P

United States Patent [19]

Angus et al.

[11] Patent Number: Plant 9,531

[45] Date of Patent: Apr. 30, 1996

[54] *CHAMELAUCIUM UNCINATUM*—'CASCADE JEWEL'

[75] Inventors: Timothy P. Angus, Faulconbridge; Nicholas F. Derera, Winston Hills, both of Australia

[73] Assignee: Newports Nurseries, Australia

[21] Appl. No.: 405,212

[22] Filed: Mar. 16, 1995

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—Christie, Parker & Hale

[57] ABSTRACT

A new and distinct variety of *Chamelaucium uncinatum* plant, named 'Cascade Jewel', particularly characterized by having an erect plant of higher than normal branching density with numerous secondary stems of gracefully weeping poise. The heavily blooming plant flowers in winter, with presentations of unusually large flowers having a wide range of nectary color from yellow-green when immature to greyed-purple when mature. The widely ranging petal colors fall within a range between near white to red-purple and purple complimenting the nectary coloration.

2 Drawing Sheets

BACKGROUND INFORMATION

This invention related to a new and distinct variety of *Chamelaucium uncinatum* which is referred to herein as the new variety 'Cascade Jewel'. 'Cascade Jewel' resulted from a controlled pollination breeding programme carried out by breeders T. P. Angus and N. F. Derera, both of 244 Singles Ridge Road, Winmalee, New South Wales, 2777, Australia.

'Cascade Jewel' resulted from the controlled pollination of *Chamelaucium uncinatum* variety GW15 (seed parent) by *Chamelaucium uncinatum* variety GW9 (pollen parent). 'Cascade Jewel' was selected in July 1991 on the basis of flower colour, flower size and plant habit. 'Cascade Jewel' was shown to be stable through two vegetatively propagated generations. The breeding and subsequent characterization of 'Cascade Jewel' were carried out at Winmalee, New South Wales, Australia.

'Cascade Jewel' is most notable for its predominance of immature nectary colour R.H.S. No 144C, mature petal colour R.H.S. No 77B, its large flower diameter (mean 17.6 millimeters) with intermediate floral tube outline, and its erect plant habit with cascading or weeping new growth, when grown under conditions such as 25° C. to 30° day temperature/15° to 18° night temperature with high nutrition.

'Cascade Jewel' has been vegetively propagated by means of striking plant cuttings at the above-noted location, at Winmalee, New South Wales, Australia. Examination of various 'Cascade Jewel' plants has confirmed that the combination of characteristics described herein are firmly fixed throughout successive generations.

DESCRIPTION OF THE DRAWINGS

'Cascade Jewel' is illustrated by teh accompanying photographic drawings.

DESCRIPTION OF THE NEW VARIETY

Figure 1:
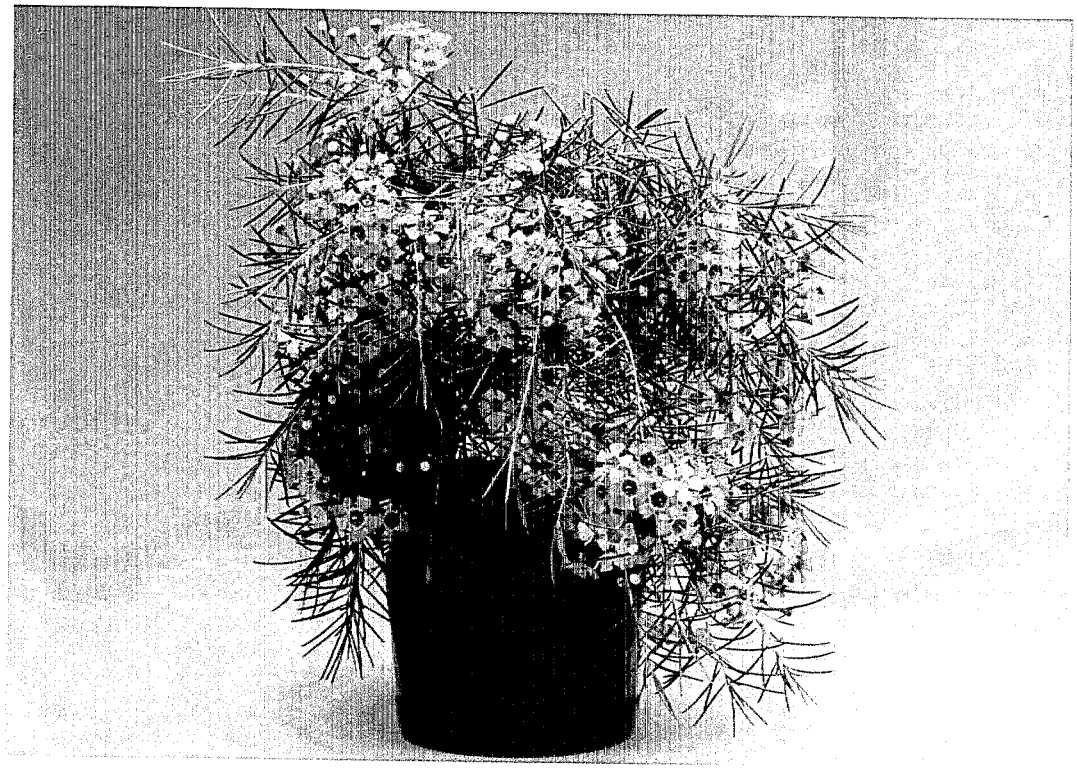
FIG. 1: Is a photographic print in full color showing a single potted specimen of 'Cascade Jewel' which was planted in approximately January 1994. The photograph was taken in June 1994 and the plant is approximately 30 centimeters high×2.5 centimeters wide.
Figure 2:
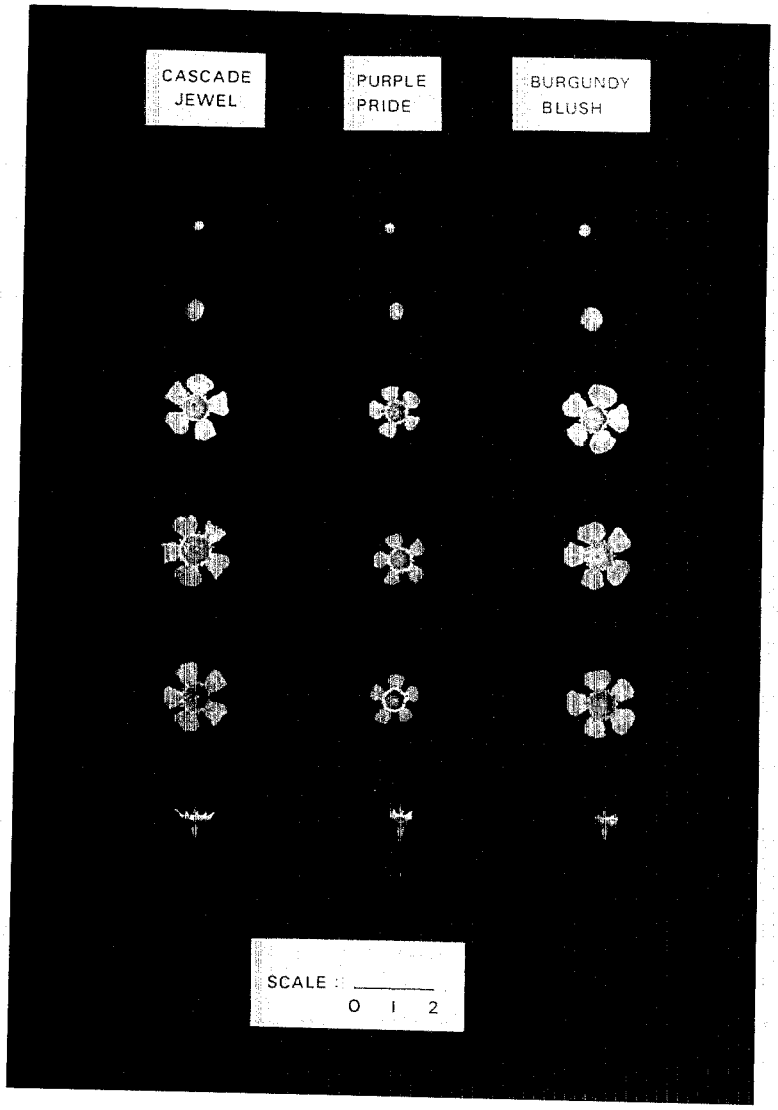
FIG. 2: Is a photographic print in full color which compares bud and flower formations of 'Cascade Jewel', and comparative *Chamelaucium uncinatum* varieties 'Purple Pride' and 'Burgundy Blush'. The figure shows the various stages from immature bud through to mature flower and floral tube outline.

The following is a detailed description of the 'Cascade Jewel' with color designations according to the *Horticultural Colour Chart* issued by the British Colour Council in collaboration with The Royal Horticultural Society Copyright 1938. The observed traits have been repeatedly observed and are believed to be characteristic of 'Cascade Jewel' which, in combination, distinguish 'Cascade Jewel' as a new and distinct cultivar.

Locality: 'Cascade Jewel' was grown and observed at Newport Nurseries, Winmalee, New South Wales, Australia Parentage: Open pollination of *Chamelaucium uncinatum* GW15 (seed parent) by *Chamelaucium uncinatum* GW9 (pollen parent).

Growth habit: Erect plant habit with cascading or weeping new growth, particularly when grown under conditions, such as 25° C. to 30° C. day/15° to 18° C. night temperatures with high nutrition.

Shape: When grown in a glasshouse with weekly nutrient supply the plants develop a semi-erect habit with new growth weeping/hanging down from the more erect firm older growth.

Size: When grown in a 130 millimeter pot in a glasshouse with nutrients supplied weekly approximate dimensions from twelve months from rooted cutting are:

Height:—60 to 75 centimeters.

Width:—20 to 35 centimeters.

Line growth: Hight branching frequency on main stem and side branch. Medium to high branching frequency on side branches.

Foliage: Mature leaflets at branched node with length 35 millimeters to 45 millimeters; diameter approximately 1.2 millimeters, opposite, linear, almost terete with acutely hooked apex, spreading to reflexed and glabrous. Colour RHS No 139A (green color group).

Flowers: Flowering times are between June through August with fifty percent burst occurring at this time. Flower diameter is approximately 18.2 millimeters (mean reading based on twenty observations), and the petal is of obovate outline. Mature flower colour is R.H.S. No 77B. The petal outline is notched and the petal margin is undulate. The predominate floral tube outline is conical.

Propagation: Propagation by cuttings.

The characteristics of 'Cascade Jewel' were compared closest known *Chamelaucium uncinatum* varieties 'Purple Pride' and 'Burgundy Blush'. Comparative growing trials were conducted in a glasshouse at Winmalee, New South Wales, Australia. Rooted cuttings were potted into a 130 millimeter pots in commericial potting mix in February 1994. Plants were watered as required. Nutrients were supplied once weekly as liquid feed and plant protection sprays were applied as necessary. The trial consisted of twenty plants of each of the cultivars 'Cascade Jewel', 'Purple Pride' and 'Burgundy Blush' randomly arranged. Pots were spaced at 24 centimeter intervals and measurements were taken from each plant in the trial for each of the characteristics recorded.

TABLE OF COMPARISON OF *CHAMELAUCIUM UNCINATUM* VARIETIES

| | CASCADE JEWEL |
|---|---|
| PLANT HABIT | Cascading |
| FLOWERING TIME (50% bud burst) | June/July/August |
| BUD COLOUR | |
| With Operculum | |
| Colour | Red |
| RHS No | 47CD 72B 50C |
| Without Operculum | |
| Colour | Purple or purple-violet |
| RHS No | 77B 81B |
| Floral tube, mid-region | |
| Colour | Yellow-green or greyed-purple or red-purple |
| RHS No | 144BC 60A 178B |
| FLOWER DIAMETER (mm) | |
| Mean | 17.6 |
| Range | 16.2–19.0 |
| PETAL | |
| Outline | Obovate |
| Immature colour | |
| Colour | Red-purple or purple or violet or white |
| RHS No | 69CD 76B 77C 84AB 155CD |
| Color Development | Fast |
| Mid-mature colour (5 to 15 days after bud burst) | |
| Colour | Purple |
| RHS No | 77BC |
| Mature Colour (ca 20 days after bud burst) | |
| Colour | Purple |
| RHS No | 77B |
| NECTARY | |
| Immature colour | |
| Colour | Yellow-green |
| RHS No | 144C |
| Mature colour | |
| Colour | Greyed-purple |
| RHS No | 187A |
| STAMINODIA | |
| Outline | Medium triangular (MT) |

-continued

TABLE OF COMPARISON OF *CHAMELAUCIUM UNCINATUM* VARIETIES

| | |
|---|---|
| Mature collar colour | |
| Colour | Red-purple |
| RHS No | 64A 67A 68A 72B |
| STYLE COLOUR | |
| Immature colour | |
| Colour | Red-purple or violet |
| RHS No | 62ABCD 73D 84C |
| Mid-mature colour | |
| Colour | Red-purple |
| RHS No | 62ABCD 73D 84C |
| Mature colour | |
| Colour | Purple |
| RHS No | 62AB 63B 68B |
| CALYX LOBE | |
| Mid-mature colour | |
| Colour | Purple |
| RHS No | 77BCD |
| Mature colour | |
| Colour | Purple |
| RHS No | 77BC |
| FLORAL TUBE | |
| Outline | Intermediate |
| Fluting | Present |
| Diameter | |
| Mean | 7.4 |
| Range | 6.5–8.0 |
| Mid-point colour | |
| Colour | Yellow-green or greyed-red |
| RHS No | 144C 178A 179A 180A 181A |
| FLOWER ARRANGEMENT | Broad distal (BD) |
| FLOWER FRAGRANCE | Present |
| | PURPLE PRIDE |
| PLANT HABIT | Erect |
| FLOWERING TIME (50% bud burst) | June/July/August |
| BUD COLOUR | |
| With Operculum | |
| Colour | Red |
| RHS No | 47AC 48A 50B |
| Without Operculum | |
| Colour | Red purple, or purple or violet |
| RHS No | 72C 75A 77BC 84B |
| Floral tube, mid-region | |
| Colour | Red or greyed-purple or green or yellow-green |
| RHS No | 53B 143C 144C 183A 184A |
| FLOWER DIAMETER (mm) | |
| Mean | 15.03 |
| Range | 13.4–16.5 |
| PETAL | |
| Outline | Obovate |
| Immature colour | |
| Colour | Purple |
| RHS No | 75AB 77D |
| Color Development | Fast |

-continued

TABLE OF COMPARISON OF
*CHAMELAUCIUM UNCINATUM* VARIETIES

| | |
|---|---|
| Mid-mature colour (5 to 15 days after bud burst) | |
| Colour | Purple or purple-violet |
| RHS No | 75A 77B 80A |
| Mature Colour (ca 20 days after bud burst) | |
| Colour | Purple or red-purple |
| RHS No | 72B 77B |
| NECTARY | |
| Immature colour | |
| Colour | Yellow-green |
| RHS No | 144B |
| Mature colour | |
| Colour | Greyed-purple |
| RHS No | 185A 187AC |
| STAMINODIA | |
| Outline | MT |
| Mature collar colour | |
| Colour | White |
| RHS No | 155D |
| STYLE COLOUR | |
| Immature colour | |
| Colour | Red-purple |
| RHS No | 62ADC |
| Mid-mature colour | |
| Colour | Red-purple |
| RHS No | 62ACD |
| Mature colour | |
| Colour | Red-purple |
| RHS No | 62D 155D |
| CALYX LOBE | |
| Mid-mature colour | |
| Colour | Red-purple or purple |
| RHS No | 67B 70B 77B |
| Mature colour | |
| Colour | Red-purple |
| RHS No | 72A 77B |
| FLORAL TUBE | |
| Outline | Conical |
| Fluting | Present |
| Diameter | |
| Mean | 7.34 |
| Range | 6.1–8.7 |
| Mid-point colour | |
| Colour | Red-purple or greyed-red |
| RHS No | 59A 178A |
| FLOWER ARRANGEMENT | BD |
| FLOWER FRAGRANCE | Present |

BURGUNDY BLUSH

| | |
|---|---|
| PLANT HABIT | Cascading |
| FLOWERING TIME (50% bud burst) | June/July/August |
| BUD COLOUR | |
| With Operculum | |
| Colour | Red |
| RHS No | 47D 48ABC |

-continued

TABLE OF COMPARISON OF
*CHAMELAUCIUM UNCINATUM* VARIETIES

| | |
|---|---|
| Without Operculum | |
| Colour | Purple |
| RHS No | 77B |
| Floral tube, mid-region | |
| Colour | Yellow-green or orange-red, or greyed-purple or red |
| RHS No | 34C 46A 144C 178A |
| FLOWER DIAMETER (mm) | |
| Mean | 17.8 |
| Range | 14.5–19.4 |
| PETAL | |
| Outline | Obovate |
| Immature colour | |
| Colour | Purple |
| RHS No | 45AC 76C 77BC |
| Color Development | Fast |
| Mid-mature colour (5 to 15 days after bud burst) | |
| Colour | Red-purple |
| RHS No | 75AB |
| Mature Colour (ca 20 days after bud burst) | |
| Colour | Red-purple |
| RHS No | 72B |
| NECTARY | |
| Immature colour | |
| Colour | Greyed-orange |
| RHS No | 167AB |
| Mature colour | |
| Colour | Greyed-purple |
| RHS No | 187A |
| STAMINODIA | |
| Outline | MT |
| Mature collar colour | |
| Colour | Red-Purple |
| RHS No | 64B 71B 72B |
| STYLE COLOUR | |
| Immature colour | |
| Colour | Red-purple |
| RHS No | 62BCD 64C 73C |
| Mid-mature colour | |
| Colour | Red-purple |
| RHS No | 62ACD 72B |
| Mature colour | |
| Colour | Red-purple |
| RHS No | 62AB 63B 64D 72B |
| CALYX LOBE | |
| Mid-mature colour | |
| Colour | Red-purple |
| RHS No | 71BD 72B |
| Mature colour | |
| Colour | Red-purple |
| RHS No | 71B 72AB |
| FLORAL TUBE | |
| Outline | Flared |
| Fluting | Present |

-continued

TABLE OF COMPARISON OF
*CHAMELAUCIUM UNCINATUM* VARIETIES

| | |
|---|---|
| Diameter | |
| Mean | 7.2 |
| Range | 6.5–78 |
| Mid-point colour | |
| Colour | Red or red-purple or greyed-red |
| RHS No | 46A 59A 178AB |
| FLOWER ARRANGEMENT | BD |

-continued

TABLE OF COMPARISON OF
*CHAMELAUCIUM UNCINATUM* VARIETIES

| | |
|---|---|
| FLOWER FRAGRANCE | Present |

We claim:

1. A new and distinct *Chamelaucium uncinatum* plant substantially as shown and described herein, distinguished principally from other varieties of its type by fower coulor, flower size, floral tube outline, and growth habit.

* * * * *